(12) United States Patent
Park et al.

(10) Patent No.: US 9,657,983 B2
(45) Date of Patent: May 23, 2017

(54) APPARATUS FOR DEFROSTING EVAPORATOR IN REFRIGERATION SYSTEM USING INFRARED EMITTING DIODE SENSOR

(71) Applicant: SINJIN ENERTEC CO., LTD., Jeollabuk-do (KR)

(72) Inventors: Jin Sup Park, Jeollabuk-do (KR); Sang Myun Park, Jeollabuk-do (KR)

(73) Assignee: SINJIN ENERTEC CO., LTD., Jeollabuk-Do (KR)

( * ) Notice: Subject to any disclaimer, the term of this patent is extended or adjusted under 35 U.S.C. 154(b) by 148 days.

(21) Appl. No.: 14/431,435

(22) PCT Filed: Aug. 1, 2014

(86) PCT No.: PCT/KR2014/006580
§ 371 (c)(1),
(2) Date: Mar. 26, 2015

(87) PCT Pub. No.: WO2015/030369
PCT Pub. Date: Mar. 5, 2015

(65) Prior Publication Data
US 2015/0247663 A1    Sep. 3, 2015

(30) Foreign Application Priority Data

Aug. 26, 2013 (KR) .................. 10-2013-0100895
Feb. 17, 2014 (KR) .................. 10-2014-0017681

(51) Int. Cl.
| | | |
|---|---|---|
| F25B 47/00 | (2006.01) |
| F25D 21/00 | (2006.01) |
| F25D 21/02 | (2006.01) |
| G01J 5/02 | (2006.01) |
| G01N 21/35 | (2014.01) |

(Continued)

(52) U.S. Cl.
CPC .......... *F25D 21/006* (2013.01); *F25D 21/02* (2013.01); *G01J 5/02* (2013.01); *G01N 21/35* (2013.01);
(Continued)

(58) Field of Classification Search
CPC ........... F25B 2700/11; F25B 2700/111; F25B 47/006; F25B 2347/023; F25D 21/006;
(Continued)

(56) References Cited

U.S. PATENT DOCUMENTS 4,109,481 A * 8/1978 Peek ................. G01B 11/0616
                                                           340/580
4,593,533 A * 6/1986 Alsenz .................... F25D 21/02
                                                           250/340

(Continued)

FOREIGN PATENT DOCUMENTS

JP    2007-271168    10/2007
JP    5178782       4/2013

(Continued)

OTHER PUBLICATIONS

International Search Report with English translation dated Sep. 24, 2014 from International Application No. PCT/KR2014/006580, pp. 1-5.

*Primary Examiner* — Jonathan Bradford
(74) *Attorney, Agent, or Firm* — MH2 Technology Law Group, LLP

(57) ABSTRACT

An apparatus for defrosting an evaporator in a refrigeration system using an infrared emitting diode includes i) a frost detection sensor configured to receive a frost sensing signal from an output part of a control processor and to transmit a frost detection signal into an input part of a control processor, wherein the frost detection signal is generated by projecting infrared to the frost and receiving reflection- (Continued)

infrared from the frost; ii) a control processor configured to convert the frost detection signal into a digital signal in the signal converting part, to evaluate if the frost detection signal is higher than a threshold value which is set from a signal setting part, and to transmit the operation signal to the defroster, as well as the display signal to the signal display part; and iii) a defroster.

4 Claims, 6 Drawing Sheets

(51) Int. Cl.
    *H01L 33/00*     (2010.01)
    *G01N 21/3554*     (2014.01)
    *G01N 21/3563*     (2014.01)
    *G01N 21/359*     (2014.01)

(52) U.S. Cl.
    CPC ....... *G01N 21/359* (2013.01); *G01N 21/3554* (2013.01); *G01N 21/3563* (2013.01); *H01L 33/00* (2013.01); *F25B 2700/111* (2013.01); *G01N 2201/062* (2013.01)

(58) Field of Classification Search
    CPC ............... F25D 21/02; F24F 2011/0087; F24F 2011/0089; F24F 2011/009
    See application file for complete search history.

(56) References Cited

U.S. PATENT DOCUMENTS

| | | | | | |
|---|---|---|---|---|---|
| 4,615,179 | A | * | 10/1986 | Chiu | F25D 21/006 62/129 |
| 4,831,833 | A | * | 5/1989 | Duenes | F25D 21/02 62/140 |
| 5,513,495 | A | * | 5/1996 | West | B67D 3/0009 222/146.6 |
| 2003/0074906 | A1 | * | 4/2003 | Marques | F25D 21/02 62/125 |
| 2012/0023974 | A1 | * | 2/2012 | Park | F25D 21/006 62/80 |
| 2013/0031921 | A1 | * | 2/2013 | Hamada | F24F 13/222 62/155 |
| 2013/0081415 | A1 | * | 4/2013 | Kim | F25D 21/006 62/129 |
| 2013/0081416 | A1 | * | 4/2013 | Kim | F25D 21/006 62/151 |
| 2013/0086928 | A1 | * | 4/2013 | Cho | F25D 21/006 62/80 |

FOREIGN PATENT DOCUMENTS

| KR | 10-0973070 | 7/2010 |
|---|---|---|
| KR | 10-2013-0036858 | 4/2013 |

\* cited by examiner

APPARATUS FOR DEFROSTING EVAPORATOR IN REFRIGERATION SYSTEM USING INFRARED EMITTING DIODE SENSOR

This is a national phase application of PCT/KR2014/006580 filed on Aug. 1, 2014, claiming to Korean Patent Application No. 10-2013-100895 filed on Aug. 26, 2013 and Korean Patent Application No. 10-2014-17681 filed on Feb. 17, 2014, the contents of which are incorporated herein by references.

TECHNICAL FIELD

The present invention relates to an apparatus for defrosting the evaporator in refrigeration system operated by following steps, comprising i) detecting the frost formed on the evaporator equipped in refrigerator, cold storage, freezing storage or heat pump using infrared emitting diode sensor; ii) transmitting the signal to the defrost system from control processor; and iii) defrosting the evaporator by operating defrosting system.

On the other hand, the present PCT application herein claims 2 convention priorities of Korean Patent Application No. 10-2013-100895 'Apparatus for defrosting evaporator in refrigeration system using infrared emitting diode sensor' filed on Aug. 26, 2013 as well as Korean Patent Application No. 10-2014-17681 'Apparatus for defrosting evaporator in refrigeration system using infrared detecting sensor' filed on Feb. 17, 2014.

DESCRIPTION OF PRIOR ART

In refrigerator, cold storage, freezing storage or heat pump, the refrigerant has been used for cooling the space through circulation and heat exchange. Conventionally, cooling has been made by circulation of 4 steps of cooling cycle, that are, compression of refrigerant, condensation, expansion and evaporation accompanied with heat exchange. Therefore, compressor, condenser, expansion valve and evaporator have been equipped in the refrigeration system.

4 steps of cooling cycle can be explained as follows. The gas phase of refrigerant has been compressed in the compressor, the compressed refrigerant has been cooled in the condenser by the heat exchange with ambient air, the flow of liquid phase of cooled refrigerant has been adjusted and expanded at the expansion valve, and the liquid phase of refrigerant has been evaporated into the gas phase in the evaporator, where the ambient heat has been absorbed for evaporation. Finally, cooled air can be supplied into storage chamber or cooling space in the refrigeration system.

Further, the gas phase of refrigerant from the evaporator has been circulated into compressor. Thereafter, the cooling cycle has been circulated and repeated from the compressor. The temperature of surface of evaporator becomes lower according to the absorption of ambient heat in the space surrounded by evaporator. Therefore, the condensed moisture shall appear on the surface of evaporator due to the relatively hot and humid ambient air, which causes the formation of frost on the surface of evaporator.

Further, the frost formed on the surface of evaporator becomes thicker by the lapse of time. Accordingly, the efficiency of heat exchange with ambient air becomes lower, which causes the decline of cooling efficiency as well as the excessive consumption of electric power.

Conventionally, to solve such problems, the timer has been equipped in the refrigeration system for measuring the cumulative operation time of compressor. After lapse of threshold cumulative operation time, the defrosting has been carried out by operating the heat supply part around evaporator.

However, in case of such conventional defrosting, the defrosting has to be carried out periodically by the lapse of threshold cumulative operation time without measuring the amount of frost formed on tire surface of evaporator. Therefore, it has the handicaps for effective removal of frost formed on the surface of evaporator. Further, it also requires unnecessary consumption of electric power as well as the increase of temperature according to the defrosting operation.

To overcome such handicaps, in Korean early publication No. 10-2011-88745 'Cooling apparatus and method for detecting the frost', it has been disclosed that the frost is detected and measured by electric sensor, and that the frost is removed according to the signal from the electric sensor.

According to said patent disclosure, the detection of frost has been measured by electric capacity between cooling pin using a number of sensors. Further, the amount of frost has been calculated and measured by the amount of electric capacity. However, in spite of the relative complexity of detection method, the detection signal cannot be considered as reliable because noise signal may be included in detection signal.

On the other hand, in Korean early publication No. 10-2013-143452 'Frost sensing device and method', it has been disclosed that the formation of frost on the evaporator is detected and measured through reflection of infrared, which comprises the steps of: emitting the infrared from the infrared emission part; reflecting the infrared on the frost; and measuring the reflected infrared at the infrared receiving part.

However, the sensitivity of infrared reflected from frost can be varied according to the conditions of medium, in case that the infrared is emitted from emission part and the reflected infrared is received and measured at infrared receiving part. Further, the absorption of infrared can be differently made according to the kind of medium. Of course, the density deviation of infrared from the infrared generator can be present even though same density of infrared is emitted from infrared emission part, which results in the discrepancies of detection sensitivity.

For completely removing the deviation or error incurred in frost detection sensor in the course of generating and receiving infrared, the inventors of present application have developed an apparatus for defrosting evaporator in refrigeration system using infrared emitting diode sensor, which is operated by following steps comprising: i) generating and projecting infrared from infrared emitting diode (D1) to evaporator under standard voltage; ii) projecting detection-infrared and receiving reflection-infrared at infrared emitting diode (D2) for measuring the voltage applied to infrared emitting diode (D2); iii) evaluating the thickness of frost on the evaporator at control processor from the declined voltage applied to infrared emitting diode (D2) which results from infrared interference and photoelectric effect; and iv) operating the defrost system, when the thickness of frost is higher than threshold value.

Problem to be Solved

The problem to be solved is to develop an apparatus for defrosting evaporator in refrigeration system using infrared emitting diode sensor for completely removing the deviation or error incurred in frost detection sensor in the course of generating and receiving infrared. Further, the apparatus for defrosting evaporator in refrigeration system can be operated by following steps comprising: i) generating and projecting infrared from infrared emitting diode (D1) to evaporator under standard voltage; ii) projecting detection-infrared and receiving reflection-infrared at infrared emitting diode (D2) for measuring the voltage applied to infrared emitting diode (D2); iii) evaluating the thickness of frost on the evaporator at control processor from the declined voltage applied to infrared emitting diode (D2) which results from infrared interference and photoelectric effect; and iv) operating the defrost system, when the thickness of frost is higher than threshold value.

Means for Solving the Problem

The object of present invention is to provide an apparatus for defrosting an evaporator in refrigeration system using infrared emitting diode sensor comprising: i) a frost detection sensor (50) configured to receive the frost sensing signal from the output part of a control processor (60), and to transmit the frost detection signal into the input part of a control processor (60), wherein the frost detection signal is generated by projecting infrared to the frost and projecting and receiving reflection-infrared from the frost; ii) a control processor (60) configured to convert the frost detection signal into digital signal in the signal converting part, to evaluate if the frost detection signal is higher than threshold value which is set from signal setting part (61), and to transmit the operation signal to the defroster (70) as well as the display signal to the signal display part (62); and iii) a defroster (70) configured to be operated depending on the signal from the control processor (60).

Further, said frost detection sensor (50) is operated by following steps comprising: i) projecting the infrared from infrared emitting diode (D1) to evaporator under standard voltage (V1) at infrared emitting part (51); ii) projecting detection-infrared and receiving reflection-infrared at infrared emitting diode (D2) in infrared receiving part (52) wherein the signal voltage (V2) applied to infrared emitting diode (D2) is declined compared to standard voltage due to infrared interference and photoelectric effect; and iii) measuring the signal voltage.

Further, the measured signal voltage (V2) is not declined in case that frost (40) is not formed on the evaporator (20) because the detection-infrared can be projected without infrared interference, while the measured signal voltage (V2) is declined in case that frost (40) is formed on the evaporator (20) because the detection-infrared is hardly projected due to infrared interference between detection-infrared and reflection-infrared from frost.

As an another embodiment of frost detection sensor (50), the frost detection sensor (50) can be operated by following steps comprising: i) projecting the infrared from infrared emitting diode (D1) to evaporator under standard voltage (V1) at infrared emitting part (51); ii) projecting detection-infrared and receiving reflection-infrared at transistor (TR) in infrared receiving part (52) wherein the signal voltage (V2) applied to transistor (TR) is declined compared to standard voltage (V1) due to infrared interference and photoelectric effect; and iii) measuring the signal voltage.

Further, a control processor (60) comprises i) a signal setting part (61) in which defrost mode, defrost time, defrost method, defrost sensitivity, frost formation sensitivity and/or compulsory defrost period can be input and set; and ii) a signal display part (62) in which setting defrost mode, setting defrost time, setting defrost method and/or alarm signal for defrosting evaporator can be displayed.

Further, the wavelength of said infrared is 800~950 nm and the standard voltage (V1) in infrared emitting diode (D1) at infrared emitting part (51) is 5V.

Advantageous Effect

The advantageous effect of present invention is to provide an apparatus for defrosting evaporator in refrigeration system using infrared emitting diode sensor for completely removing the deviation or error incurred in frost detection sensor in the course of generating and receiving infrared. Further, the apparatus for defrosting evaporator in refrigeration system can be operated by following steps comprising: i) generating and projecting infrared from infrared emitting diode (D1) to evaporator under standard voltage; ii) projecting detection-infrared and receiving reflection-infrared at infrared emitting diode (D2) for measuring the voltage applied to infrared emitting diode (D2); iii) evaluating the thickness of frost on the evaporator at control processor from the declined voltage applied to infrared emitting diode (D2) which results from infrared interference and photoelectric effect; and iv) operating the defrost system, when the thickness of frost is higher than threshold value.

The other advantageous effect of present invention is to minimize the operation time of defroster, because the operation of defroster is stopped by the real-time signal from the control processor at the time of removing frost on the evaporator. Of course, the cost of defrost can be saved efficiently according to the minimized operation time.

Figure 1:
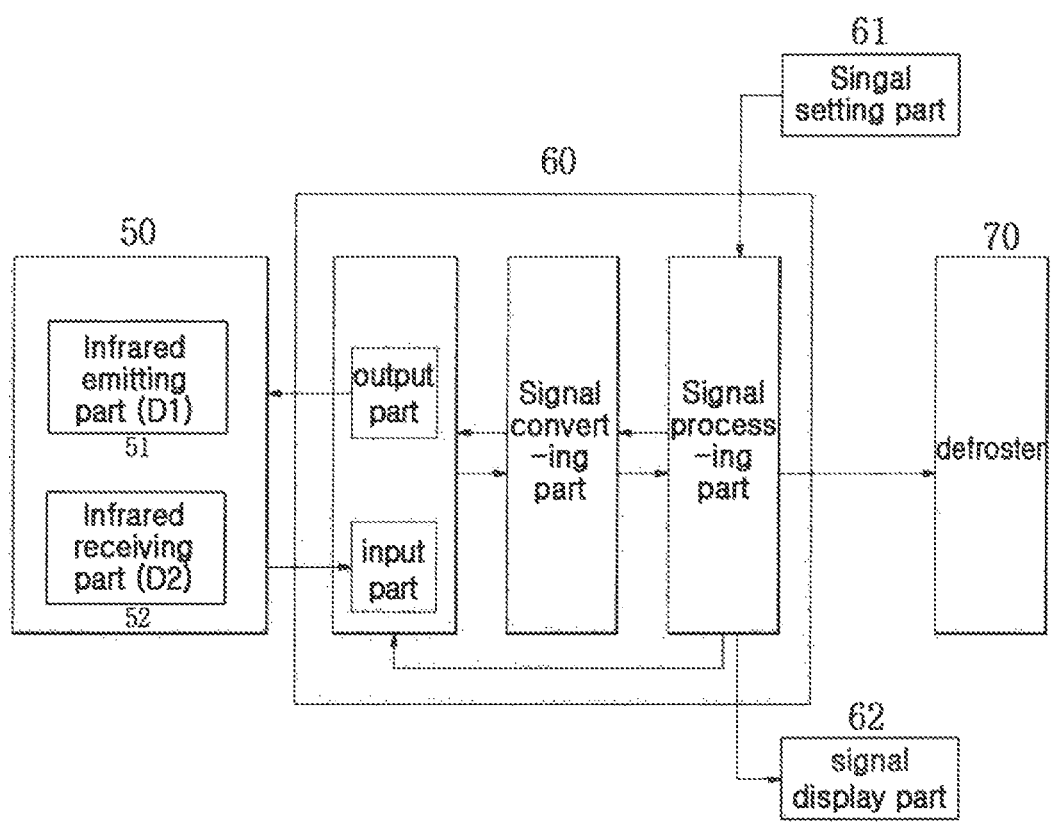
FIG. 1 is a block diagram indicating the construction of a frost detection sensor, a control processor and a defroster in the present invention. A control processor (60) includes a signal setting part (61) in which defrost mode, defrost time, defrost method, defrost sensitivity, frost formation sensitivity and/or compulsory defrost period can be input and set; and a signal display part (62) in which setting defrost mode, setting defrost time, setting defrost method and/or alarm signal for defrosting evaporator can be displayed.

| Description of reference numeral | | |
|---|---|---|
| 10. Cooling device | 20. Evaporator | 30. Frost |
| 40. Reflection of infrared | 50. Frost detection sensor | 51. Infrared emitting part (D1) |
| 52. Infrared receiving part (D2) | 60. Control processor | 70. Defroster |
| 100. Evaporation pipe in evaporator | 110. Evaporation pin | |

PREFERRED EMBODIMENT OF INVENTION

The present invention relates to an apparatus for defrosting an evaporator in refrigeration system using infrared emitting diode sensor comprising: i) a frost detection sensor (50) configured to receive the frost sensing signal from the output part of a control processor (60), and to transmit the frost detection signal into the input part of a control processor (60), wherein the frost detection signal is generated by projecting infrared to the frost and projecting and receiving reflection-infrared from the frost; ii) a control processor (60) configured to convert the frost detection signal into digital signal in the signal converting part, to evaluate if the frost detection signal is higher than threshold value which is set from signal setting part (61), and to transmit the operation signal to the defroster (70) as well as the display signal to the signal display part (62); and iii) a defroster (70) configured to be operated depending on the signal from the control processor (60).

The present invention can be explained more specifically in reference to attached drawings.

FIG. 1 is a block diagram indicating the construction of a frost detection sensor, a control processor and a defroster in the present invention.

The control processor (60) is a key element of the construction of present invention. The frost detection sensor (50) is connected with control processor (60) for communicating electric signals. Further, the defroster (70) is also connected with control processor in order to be operated for defrosting the evaporator.

The frost detection sensor (50) includes infrared emitting part and infrared receiving part, which is connected with control processor (60) for communicating electric signals. The infrared is generated and projected from infrared emitting diode (D1) in infrared emitting part (51) under standard voltage, preferably 5V, into the evaporator (20). The detection-infrared is also generated and projected from infrared emitting diode (D2) in infrared receiving part (52) for measuring the signal voltage applied to infrared emitting diode (D2), which is declined compared to standard voltage due to infrared interference and photoelectric effect. Then, the measured signal in frost detection sensor is transmitted into control processor (60).

Further, the analog voltage signal from the frost detection sensor is filtered and converted into the digital signal in the signal converting part of control processor (60). Then, if digital signal is higher than threshold value of frost, the operation signal from control processor is transmitted into defroster (70).

Further, a control processor (60) includes a signal setting part (61) in which defrost mode, defrost time, defrost method, defrost sensitivity, frost formation sensitivity and/or compulsory defrost period can be input and set; and a signal display part (62) in which setting defrost mode, setting defrost time, setting defrost method and/or alarm signal for defrosting evaporator can be displayed.

Finally, the frost formed on evaporator in refrigeration system has been defrosted by the operation of defroster (70), which is operated by the signal from the control processor (60). Of course, any kinds of defroster can be available, if the heating apparatus can defrost the evaporator.

Figure 2:
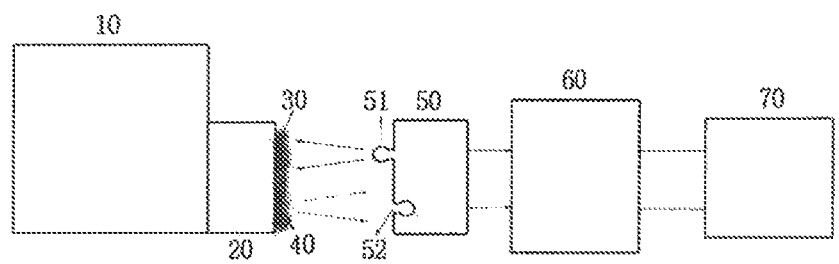
FIG. 2 shows the schematic view of defroster system in the present invention.

FIG. 2 shows the schematic view of defroster system in the present invention.

As shown in FIG. 2, the frost detection sensor can measure the infrared interference signal alter projecting the infrared from infrared emitting part (51) to evaporator (20), reflecting the infrared (40) from the frost formed on evaporator and detecting and measuring the infrared interference at infrared receiving part (52).

The wavelength of said infrared is in the range of 800~950 nm.

Figure 3A:
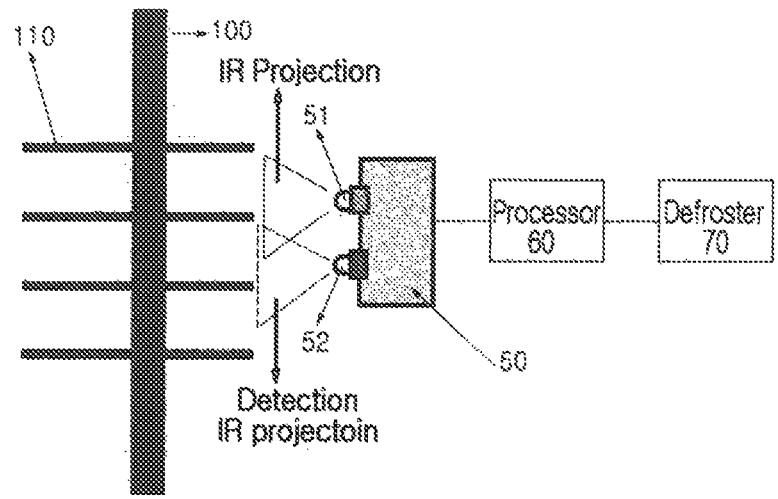
FIG. 3a shows the detailed view indicating the infrared projection at infrared emitting part (51) as well as the detection-infrared projection at infrared receiving part (52) in case that frost is not formed on the evaporator.

FIG. 3a shows the detailed view indicating the infrared projection at infrared emitting part (51) as well as the detection-infrared projection at infrared receiving part (52) in case that frost is not formed on the evaporator.

If the frost is not formed on the evaporator, the infrared projected from infrared emitting part (51) is absorbed at evaporation pipe (100) or evaporation pin (110) in the evaporator. Therefore, infrared is not reflected from evaporator. Further, detection-infrared projected from infrared receiving part (52) is projected without any interference. Therefore, the voltage of infrared emitting diode (D2) in infrared receiving part (52) shall be same as the voltage of infrared emitting diode (D1) in infrared emitting part (51). The voltage of infrared emitting diode (D1) is preferably 5V.

Figure 3B:
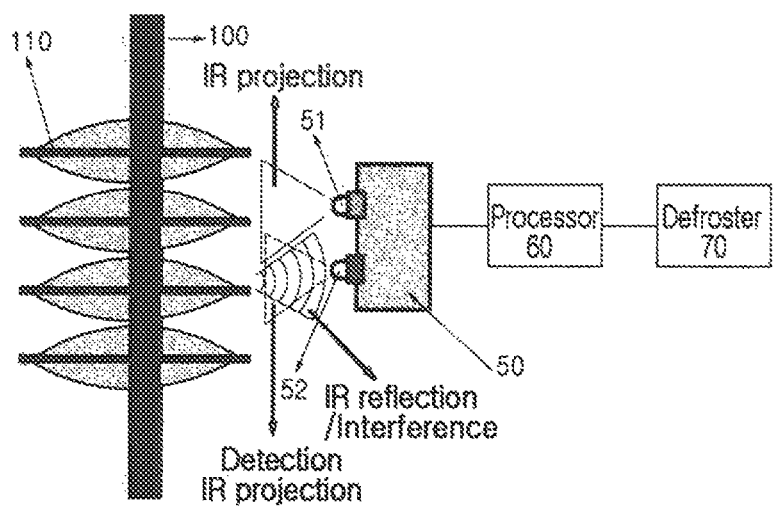
FIG. 3b shows the detailed view indicating the infrared projection at infrared emitting part (51) as well as the detection-infrared projection at infrared receiving part (52) in case that frost is formed on the evaporator. The infrared interference can occur between detection-infrared from infrared receiving part and reflection-infrared from frost.

FIG. 3b shows the detailed view indicating the infrared projection at infrared emitting part (51) as well as the detection-infrared projection at infrared receiving part (52)

in case that frost is formed on the evaporator. The infrared interference can occur between detection-infrared from infrared receiving part and reflection-infrared from frost.

If the frost is formed on the evaporator, the infrared projected from infrared emitting part (51) is reflected from the frost on the evaporator. Therefore, infrared is reflected from evaporator. Further, detection-infrared projected from infrared receiving part (52) can have the interference with the infrared reflected from frost. Therefore, the voltage of infrared emitting diode (D2) in infrared receiving part (52) shall be declined than the voltage of infrared emitting diode (D1) in infrared emitting part (51) due to the infrared interference.

Figure 3C:
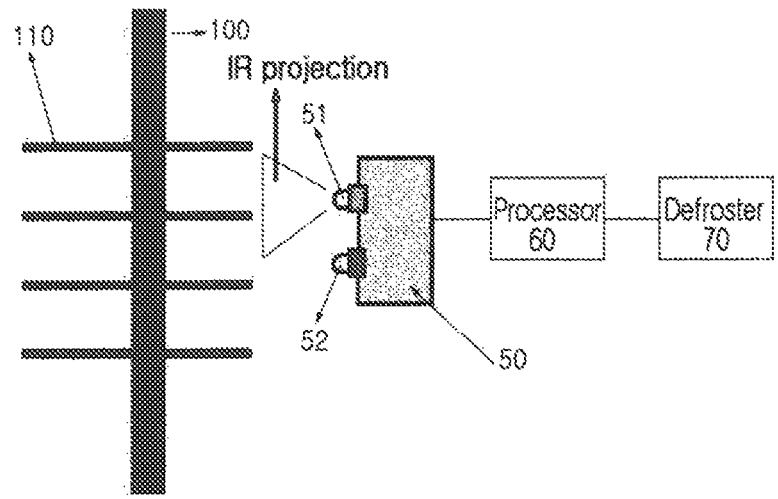
FIG. 3c shows another view as to another embodiment of frost detection sensor, in case that frost is not formed on the evaporator. The infrared is projected from infrared emitting part (51) and the projected infrared is not reflected from evaporator in case that frost is not formed on the evaporator. Therefore, reflected infrared cannot be detected at infrared receiving part (52).

FIG. 3c shows another view as to another embodiment of frost detection sensor, in case that frost is not formed on the evaporator.

The infrared is projected from infrared emitting part (51) and the projected infrared is not reflected from evaporator in case that frost is not formed on the evaporator. Therefore, reflected infrared cannot be defected at infrared receiving part (52). Accordingly, voltage generation cannot occur caused by reflected infrared.

Figure 3D:
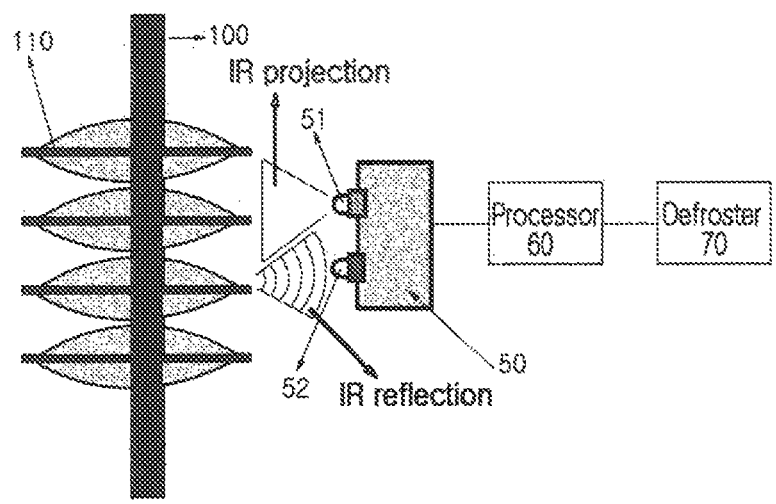
FIG. 3d shows another view as to another embodiment of frost detection sensor, in case that frost is formed on the evaporator. The infrared is projected from infrared emitting part (51) and the projected infrared is reflected from the frost on the evaporator in case that frost is formed on the evaporator. Therefore, reflected infrared can be detected by voltage generation at transistor (TR) in infrared receiving part (52).

FIG. 3d shows another view as to another embodiment of frost detection sensor, in case that frost is formed on the evaporator.

The infrared is projected from infrared emitting part (51) and the projected infrared is reflected from the frost on the evaporator in ease that frost is formed on the evaporator. Therefore, reflected infrared can be detected by voltage generation at transistor (TR) in infrared receiving part (52).

Figure 4A:
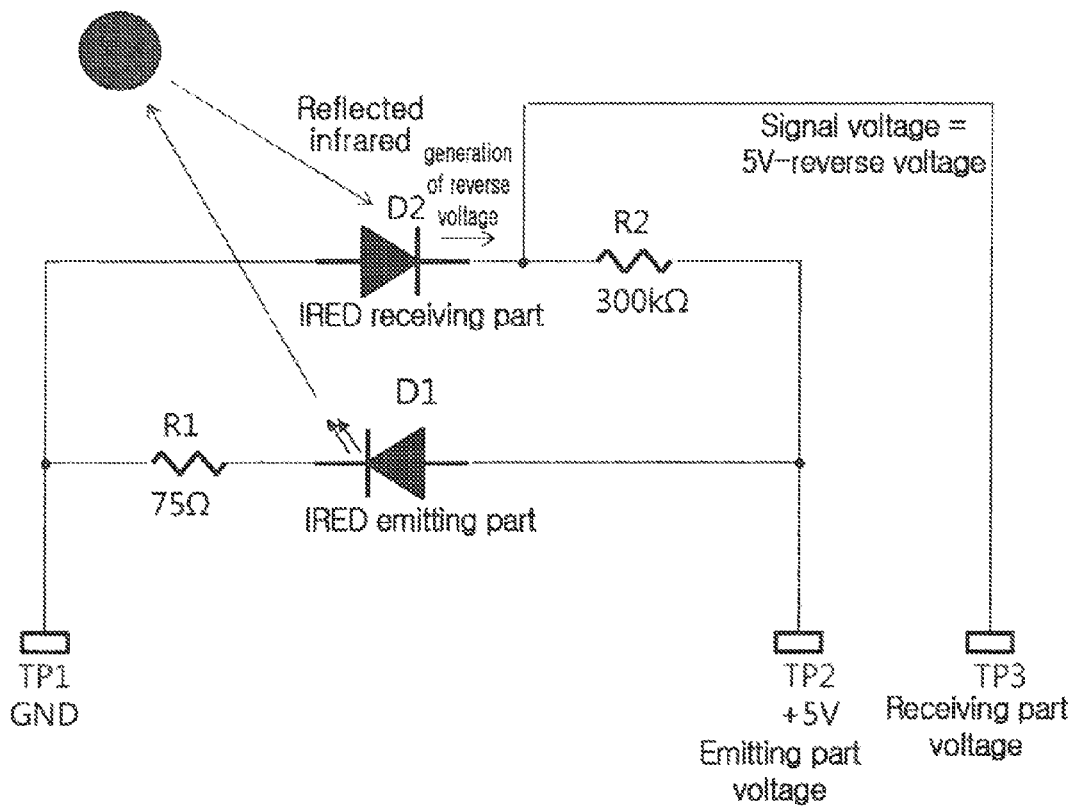
FIG. 4a shows the circuit constructing infrared emitting part (51) and infrared receiving part (52) in the frost detection sensor. Infrared emitting diode (D1) in infrared emitting part is applied to standard voltage (5V) and infrared emitting diode (D2) in infrared receiving part is applied to signal voltage (5V-reverse voltage).

FIG. 4a shows the circuit constructing infrared emitting part (51) and infrared receiving part (52) in the frost detection sensor.

Infrared emitting diode (D1) in infrared emitting part is applied to standard voltage (5V) and infrared emitting diode (D2) in infrared receiving part is applied to signal voltage (5V-reverse voltage). According to increase of reflected infrared, the reverse voltage also increases, which results in the decline of signal voltage at infrared emitting diode (D2). Therefore, the voltage of infrared emitting diode (D2) in infrared receiving part (52) shall be declined than the voltage (5V) of infrared emitting diode (D1) in infrared emitting part (51) due to the infrared interference.

On the other hand, if the frost is not formed, the infrared is not reflected, which cannot result in reverse voltage generation. Therefore, the signal voltage in infrared receiving part shall be same as standard voltage in infrared emitting part.

Figure 4B:
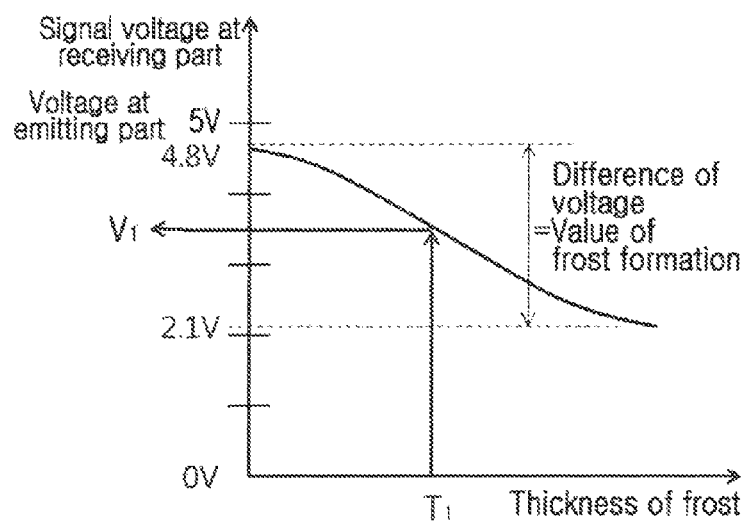
FIG. 4b shows the graph indicating the relationship between the signal voltage measured at infrared receiving part in frost defection sensor and the thickness of frost. According to increase of frost thickness, the signal voltage at infrared receiving part is declined due to the reverse-voltage generation. The threshold thickness of frost is represented by $T_1$ and the signal voltage measured at this thickness is represented by $V_1$.
Figure 4E:
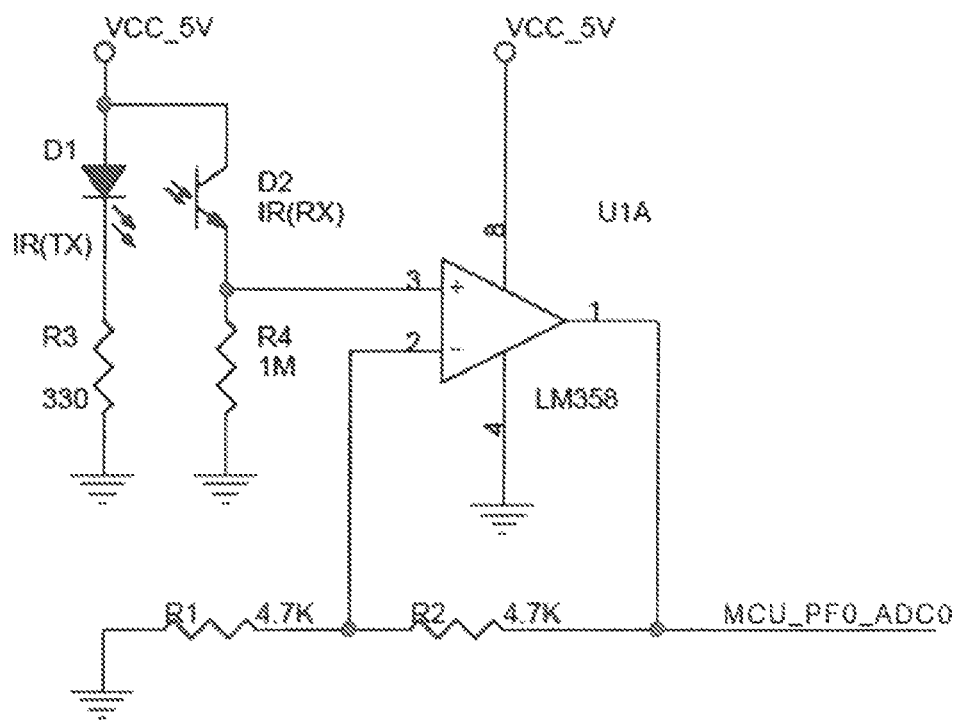
FIG. 4c shows another embodiment of circuit in another frost detection sensor. The infrared is projected from infrared emitting diode (D1) in infrared entitling part (51) to evaporator (20) under standard voltage. According to the density of reflection-infrared, the formation of frost can be measured by voltage generated at transistor (TR) in the infrared receiving part (52).

FIG. 4b shows the graph indicating the relationship between the signal voltage measured at infrared receiving part in frost detection sensor and the thickness of frost.

According to increase of frost thickness, the signal voltage at infrared receiving part is declined due to the reverse-voltage generation. The threshold thickness of frost is represented by $T_1$ and the signal voltage measured at this thickness is represented by $V_1$.

Of course, the threshold thickness of frost $T_1$ can be measured by signal voltage $V_1$ at infrared receiving part. Further, signal voltage $V_1$ also can be set at the control processor (60) through the setting in signal setting part (61).

FIG. 4c shows another embodiment of circuit in another frost detection sensor.

In another embodiment of circuit, the transistor is replaced for measuring voltage instead of infrared emitting diode (D2) in preferred embodiment.

The infrared is projected from infrared emitting diode (D1) in infrared emitting part (51) to evaporator (20) under standard voltage. According to the density of reflection-infrared, the formation of frost can be measured by the voltage generated at transistor (TR) in the infrared receiving part (52).

Figure 5:
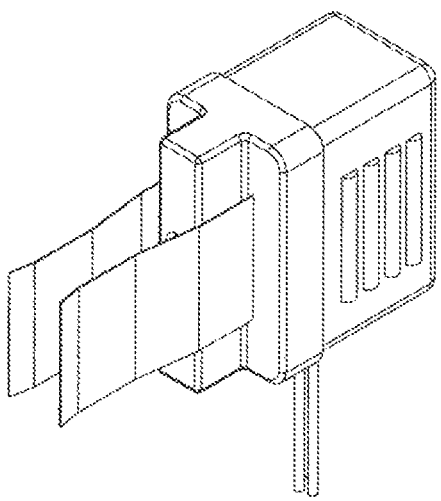
FIG. 5 shows a schematic view of frost detection sensor. The frost detection sensor includes right and left attaching segment in front of sensor to be attached at the pin of evaporator.

FIG. 5 shows a schematic view of frost detection sensor. The frost detection sensor includes right and left attaching segment in front of sensor to be attached at the pin of evaporator.

Further, the frost detection sensor (50) includes infrared emitting part containing infrared emitting diode (D1) and infrared receiving part containing infrared emitting diode (D2).

Figure 6:
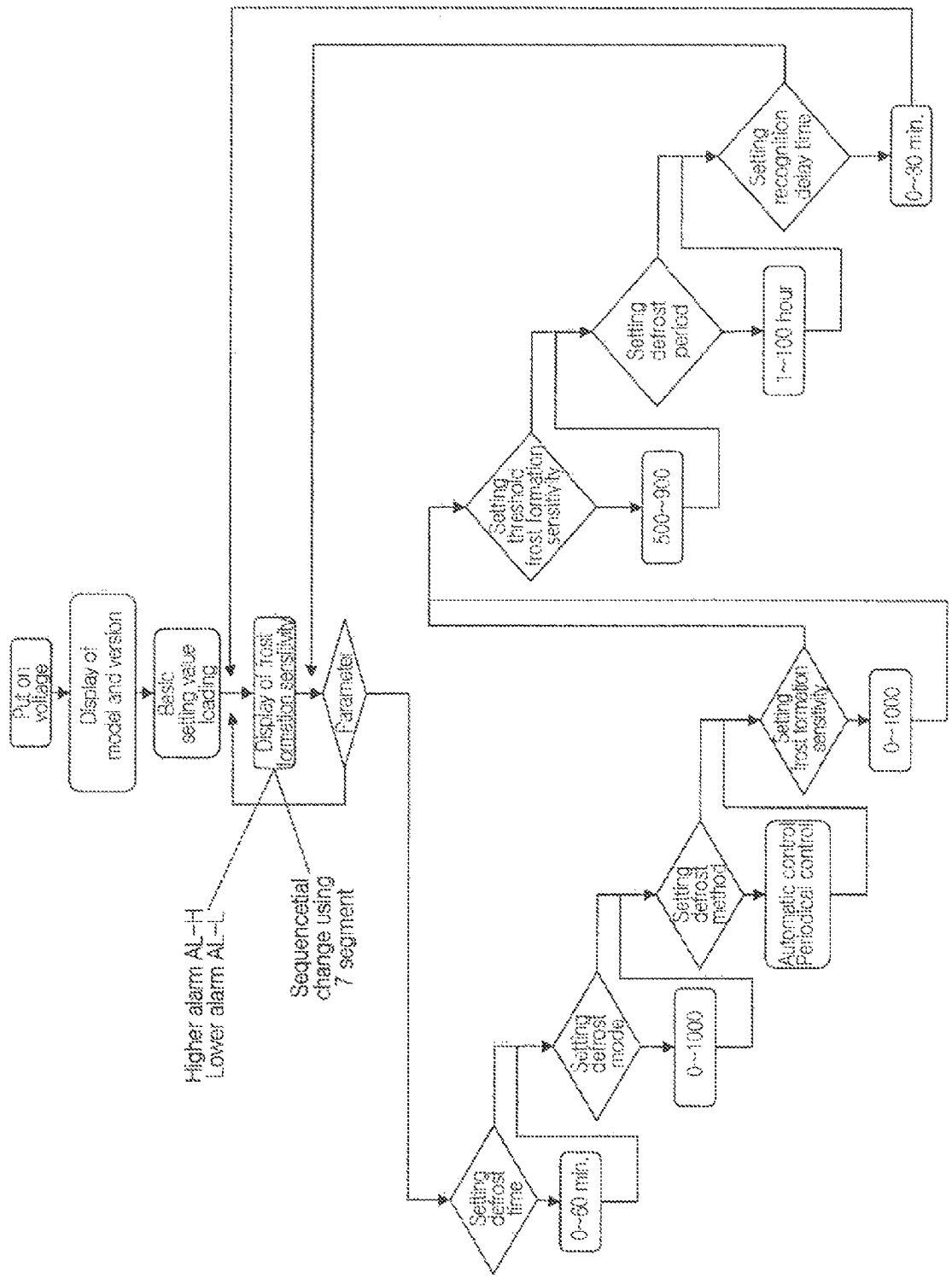
FIG. 6 shows a flow chart indicating the setting operation conditions of defroster in the control processor of present invention. According to the setting operation conditions, the defroster is operated by the signal from the control processor.

FIG. 6 shows a flow chart indicating the setting operation conditions of defroster in the control processor of present invention. According to the setting operation conditions, the defroster is operated by the signal from the control processor.

The control processor (60) includes a signal setting part (61) in which defrost mode, defrost time, defrost method, defrost sensitivity, frost formation sensitivity and/or compulsory defrost period can be input and set; and a signal display part (62) in which setting defrost mode, setting defrost time, setting defrost method and/or alarm signal for defrosting evaporator can be displayed.

In this figure, the procedure for setting the defrost time, defrost mode, defrost method and frost formation sensitivity has been illustrated. Further, the procedure for setting the threshold frost formation sensitivity, defrost period and recognition delay time has been also illustrated.

Further, if the signal over threshold value is transmitted from frost detection sensor (50) to control processor (60), the defroster (70) will be operated in accordance with the operation signal from control processor based upon the installed program. After complete removal of frost, defroster will be stopped in response to the signal detected from frost detection sensor (50).

Further, the invention can minimize the operation time of defroster, because the operation of defroster is stopped by the real-time signal from the control processor at the time of removing frost on the evaporator. Of course, the cost of defrost can be saved efficiently according to the minimized operation time.

What is claimed is:

1. An apparatus for defrosting an evaporator in a refrigeration system using an infrared emitting diode sensor, the apparatus comprising:
   i) a frost detection sensor configured to receive a frost sensing signal from an output part of a control processor, and to transmit a frost detection signal into an input part of the control processor, wherein the frost detection signal is generated by projecting infrared radiation to frost and receiving reflection-infrared from the frost, wherein the frost detection sensor comprises a first infrared emitting diode (D1) configured to project the infrared radiation toward the evaporator under a standard voltage (V1) at an infrared emitting part; and a second infrared emitting diode (D2) configured to receive reflection-infrared from the evaporator at an infrared receiving part,
   wherein the frost is detected by measuring a signal voltage (V2) at the second infrared emitting diode (D2) that is lower than the standard voltage (V1);
   ii) the control processor configured to convert the frost detection signal into a digital signal in a signal converting part, to evaluate if the frost detection signal is higher than a threshold value which is set from a signal setting part, and to transmit an operation signal to a defroster and a display signal to a signal display part; and iii) the defroster configured to be operated depending on the operation signal from the control processor.

2. The apparatus for defrosting an evaporator according to claim 1, wherein the signal voltage (V2) that is measured is not lower than the standard voltage (V1) in a case that frost is not formed on the evaporator because absence of the frost does not produce infrared radiation interference with the infrared radiation from the first infrared emitting diode (D1), and wherein the signal voltage (V2) that is measured is lower than the standard voltage (V1) in a case that frost is formed on the evaporator because the presence of the frost produces infrared radiation interference between the infrared radiation from the first infrared emitting diode (D1) and the infrared radiation scattered by the frost.

3. The apparatus for defrosting an evaporator according to claim 1, wherein the control processor comprises i) the signal setting part in which defrost mode, defrost time, defrost method, defrost sensitivity, frost formation sensitivity and/or compulsory defrost period can be input and set; and ii) the signal display part in which setting defrost mode, setting defrost time, setting defrost method and/or alarm signal for defrosting evaporator can be displayed.

4. The apparatus for defrosting an evaporator according to claim 1, wherein a wavelength of the infrared radiation is 800~950 nm and the standard voltage (V1) in the first infrared emitting diode (D1) at the infrared emitting part is 5V.

* * * * *